United States Patent [19]

Peyman et al.

[11] Patent Number: 5,258,412
[45] Date of Patent: Nov. 2, 1993

[54] VITREOUS REPLACEMENT

[76] Inventors: Gholam A. Peyman, 2020 Gravier St., Ste. B, New Orleans, La. 70112-2234; Leland C. Clark, Jr., 218 Greendali Ave., Cincinnati, Ohio 45220

[21] Appl. No.: 848,329

[22] Filed: Mar. 9, 1992

[51] Int. Cl.$^5$ ............................................. A61K 47/00
[52] U.S. Cl. ..................................... 514/772; 514/912
[58] Field of Search ................................ 514/772, 912

[56] References Cited

U.S. PATENT DOCUMENTS 4,490,351  12/1984  Clark, Jr. ................................. 424/5

OTHER PUBLICATIONS

Klinische Monatsblatter fur Augenheilkunde, 1991, vol. 199, No. 4, pp. 256-258. Lemer et al. See the entire abstract.

Japanese Journal of Ophthamology, 1991, vol. 35, No. 3, pp. 282-291. Suzuki et al. (See the entire abstract).

*Primary Examiner*—Zohreh A. Fay
*Attorney, Agent, or Firm*—Haverstock, Garrett & Roberts

[57] ABSTRACT

A vitreous substitute is disclosed which is introduced into the eye by injection in a liquid form to form a gel in the eye to replace the vitreous. The substitute comprises a silicone liquid which is allowed to gel in the eye. Methods involving the use of these gels during retinal surgery are also disclosed.

15 Claims, No Drawings

VITREOUS REPLACEMENT

BACKGROUND OF THE INVENTION

This invention relates to a biocompatible composition suitable for vitreous replacement or substitute as well as methods of treating disorders of the eye with vitreous replacement or substitute.

Clinically vitreous replacement in ophthalmology has been an important goal for clinicians for over half a century. Vitreous, the jelly-like substance which fills three-fourths of the eye, is a clear transparent material, comprised of 99% water. The vitreous provides shape to the eye, transmits light, and forms a semi-solid support for the retina against the choroid. When the vitreous is physically altered or becomes opaque as a result of hemorrhage, permanent blindness can result. For example, should the vitreous partially liquify, which often occurs with age, disease or other factors, its supporting capability is diminished and retinal detachment may ensue as a result of pulling of the retina. Furthermore, the vitreous may become opaque due to cellular infiltration or hemorrhage. Cellular infiltration is common in a number of inflammatory processes of tissue surrounding the vitreous. As a consequence of inflammation, opacification and degeneration of the vitreous occurs. Vitreous hemorrhage is also common, particularly in diabetecs. This occurs when the normal and abnormal retinal vessels rupture hence bleeding into the vitreous, which then develop into large opaque areas. Unlike most other tissue, vitreous is avascular and does not contain a significant number of scavenging macrophages. Therefore, if foreign agents or blood penetrate the vitreous, they may permanently remain in the vitreous, thereby leading to partial or total vision impairment.

Biochemically, the rigidity and viscosity of the vitreous is the result of a delicate fibril meshwork of collagen-like protein, intertwined with hyaluronic acid. Hyaluronic acid, which is responsible for the viscosity of the vitreous, is a mucopolysacharide. Its function is to keep the vitreous from separating into solid and liquid components, thus preventing the collagen from collapsing. The soluble components include glycoproteins, glucose, sodium, potassium, bicarbonate and calcium.

Vitreous replacement has been attempted over the last twenty years, mainly for the two reasons. First is the vitreous opacification produced as a result of aging, trauma, inflammation and hemorrhage. Second is the vitreous degeneration which causes traction on the retina with subsequent retinal detachment. Although such vitreous replacement with animal and human vitreous has been attempted, it has been proven not to be useful compared to other easily available substitutes which, because of their properties, could exert tamponading effects on the retina, or be simply replaced by body fluid.

Among the vitreous replacements currently used are various infusion fluids, generally applied during surgical procedure to remove the vitreous opacities (a procedure called vitrectomy). Previous investigations have demonstrated that physiologic saline solution, containing glucose, bicarbonate, potassium, and calcium is sufficient to maintain the transparency of the media and not be toxic to the lens and the cornea. A review of these substances can be found in publications by: 1) McEnerney JK and Peyman GA, Simplification of glutathione-bicarbonate-Ringer solution: Its effect on corneal thickness, *Investigative Ophthalmology & Visual Science* 1977, 16(7):657–660, and 2) Benson WE et al, Intraocular irrigating solution for pars plana vitrectomy: Prospective randomized double blind study, *Archives of Ophthalmology* 1981; 99:1013. The infusion fluids are generally used to replace the vitreous that has been opacified by hemorrhage or inflammation. Since these fluid substitutes do not exert any significant tamponading effect on the retina because of their liquidity properties, they do not provide support to the retinal structure. Furthermore, these substitutes are replaced by body fluid, generally less than one day after application.

A second application of the vitreous substitutes has been for treatment of retinal detachment. Vitreous replacement has been investigated extensively by surgery. The general technique has been the injection of replacement material, combined with prior or simultaneous drainage of the vitreous or subretinal fluid. Although irrigating solutions have been used to increase the intraocular pressure in these conditions, the solutions do not provide any tamponading effects, as mentioned previously.

However, intraocular gases have proved to be useful in vitreous and retinal detachment surgery. Postoperative hypotony (reduced intraocular pressure) and choroidal effusion can be prevented by restoring intraocular volume. Certain gases can tamponade retinal tears until a permanent chorioretinal adhesion forms to seal the retinal tear. Gases, however, have been found to have certain disadvantages, largely because of their expansion property after injection into the vitreous cavity. They can raise the intraocular pressure, causing the occlusion of central retinal artery. Furthermore, postoperative prone positioning is of importance to prevent pupillary block glaucoma. Contact of the gas with the lens can induce cataract formation, while contact between gas and corneal endothelium can cause corneal opacification. Among the gases used for vitreous substitutes are air, oxygen, nitrogen, carbon dioxide, argon, and other inert gases. The disadvantage of these gases is rapid reabsorption from the vitreous cavity, generally within one or two days. Thus its purpose as a supporting element is considerably reduced following reabsorption for the vitreous. Because of this, other gases have been explored which could expand and remain in the eye longer than air when injected in a small volume. Among these gases that have been investigated as possible temporary vitreous substitutes are sulfur hexafluoride ($SF_6$), octofluorocyclobutane ($C_4F_8$) and other perfluorocarbon gases. For a review, see publications by: 1) Vygantas CM, Peyman GA et al, Octafluorocyclobutane and other gases for vitreous replacement, *Archives of Ophthalmology* 1973; 90:235-2, 2) Taneu HL, Gas injection in the rabbit vitreous: A preliminary study, *Canadian Journal of Ophthalmology* 10972, 7:349, 3) Lincoff H et al, The perfluorocarbon gases in the treatment of retinal detachment, *Ophthalmology* 1983, 90:546–551. These substances are very useful in tamponading the retina for 7–30 days in the postoperative period, after which the gas is generally absorbed by the body fluid. After the absorption of the gas, the tamponading effect and volume expanding effect completely disappears. After this the eye must depend on its own natural mechanisms for production of intraocular fluid. Complications associated with the use of these gases include gas expansion, increased intraocular pressure, glaucoma and occlusion of central retinal artery.

Another chemical substance used for vitreous replacement is hyaluronic acid, which is naturally found in the vitreous humor cavity. Hyaluronic acid does not provide any tamponading effect on the retina during surgery or afterwards, partly because of its low surface tension and its specific gravity. It is generally absorbed into the body within 14 days after application. See Balaz EA et al, Hyaluronic acid in the replacement of vitreous and aqueous humor, *Modern Problems in Ophthalmology* 1972, 10:390. Thus in order to provide a clear vitreous substitute without volume expansion and absorption, investigators have evaluated other classes of material which could be injected into the eye. These include silicones, fluorosilicones and perfluorocarbon liquids.

Silicones are polymers of alternating silicon and oxygen atoms where the silicon atom has various organic groups attached. Polymethylsiloxanes are optically clear. Their specific gravity is less than 1 (0.9), and the viscosities of various preparations can be synthesized so as to vary between 0.65 and 60,000 cs. In ophthalmology, viscosities between 10 and 12,500 cs have been used to maintain the clarity of the vitreous and to reposition the retina. The initial work was done by Stone in 1958 (Stone W Jr. Oculoplasty in surgery of the eye. New England J of Medicine 1958; 258:486) and later in humans (Cibis Pa. Recent method in the surgical treatment of retinal detachment: Intravitreal procedures, *Transactions of the Ophthalmological Societies of the United Kingdom* 1965, 85:111. Subsequently, numerous investigators have used silicone oils with viscosities of 1000 to 12,500 cs for vitreous replacement. Because of its visco-liquidity property, silicone oil can move in the postoperative period and come in contact with the lens, causing cataract, or, in aphakic patients may contact the corneal endothelial cells, causing corneal endothelial damage. Furthermore, the silicones can emulsify in the postoperative period and migrate from the vitreous cavity into the anterior chamber and restrict or close the outflow channels for intraocular fluid. In addition, emulsified silicone oil is not optically transparent. Therefore, investigators have removed the silicone after implantation, generally between one to six months. After removal of silicone, and its replacement with physiologic saline solution or air, the body has to replace this material, again depending on its own natural regenerating power to maintain the intraocular pressure and provide intraocular support for the retina.

For a review of vitreous replacement with silicone, reference again is made to the publications by Leaver PK et al, Silicone oil injection in the treatment of massive preretinal retraction: II. Late complications in 93 eyes, *British Journal of Ophthalmology* 1979, 63:361-367, and Peyman GA et al, Randomized clinical trial of intraocular silicone vs. gas in the management of complicated retinal detachment and vitreous hemorrhage, *International Ophthalmology* 1987, 10:221-234.

Other group of synthetic materials includes perfluorocarbon liquids. Perfluorocarbon liquids were initially developed as a blood substitute. The initial studies evaluating their use as vitreous substitute was performed by Haidt et al and has been extensively reported in Clark's U.S. Pat. No. 4,490,351. Because of the high specific gravity, perfluorocarbon liquids can exert a tamponading effect on the retina when injected into the eye. Of all perfluorocarbon liquids studied thus far, only perfluorophenanthrene has been left inside the eye for a period of up to six months without causing toxic reaction to the retina and the lens. However, if perfluorocarbon liquids come in contact with the corneal endothelial cells, they can damage corneal endothelial cells within 2-3 weeks. Therefore, it should be used only in phakic eyes. In general, perfluorocarbon liquids can also emulsify between 3-6 months. However, the emulsification of perfluorocarbon liquid, although it creates a haze, is not as severe as emulsificaion of silicone. Perfluorocarbon liquids are used either during surgery (as a tool to reattach the retina) and removed immediately following surgery, or are used as temporary vitreous substitute, generally for a period of one month, to provide a tamponading effect on the retina until scar formation is achieved. Perfluorocarbons have to be eventually replaced either with physiologic saline or air, and after replacement again, the eye has to depend on its own by producing intraocular fluid to provide support for the retina.

Another synthetic material used for vitreous replacement is acrylamide gel which has been reported by Muller, Jensen K, Oculoplastic vitreous replacement with acrylamide: A preliminary report, *Modern Problems of Ophthalmology* 1974, 12:385. The use of this substance has been similar to the use of silicone in the vitreous cavity. It has been injected in small volumes to provide some support during and after surgery for retinal detachment.

As mentioned previously, all the currently available vitreous substitutes have been developed to provide a temporary support for the retina, either during surgery or in the immediate postoperative period. They are generally liquid in nature, which can diffuse from the vitreous cavity into the anterior chamber, and can cause corneal damage and opacification when they come in contact with the corneal endothelium cells. Furthermore, after their removal, which becomes imperative because of the emulsification and migration, hypotony occurs. Hypotony often is a common complication after vitrectomey, specifically after traumatic eye injuries or related reoperation for retinal detachment. Eyes with either preexisting hypotony, severe trauma, prolonged surgical procedure or preoperative inflammation, appear more susceptible to development of chronic hypotony after a vitrectomy. Medical treatment of hypotony includes the use of topical steroids to decrease any associated intraocular inflammation. Surgical methods to treat hypotony include application of diathermy over the possible cyclodialysis cleft to block the exit of intraocular fluid and prevent rapid flow of intraocular fluid toward the choroid.

Temporary use of the hyaluronic acid maintains the intraocular pressure for a period of two weeks, while certain gases can maintain the intraocular pressure for a month. However, after their absorption, the eye becomes hypotonic with subsequent shrinking of the globe and collapse of the sclera. Generally, this complication is accompanied by exudative detachment of the retina and, with time, the retina disorganizes. Because of loss of corneal clarity, the vision is completely lost.

SUMMARY OF THE INVENTION

This invention is concerned with the use of compatible substances which can be injected into the vitreous cavity of the eye in a liquid form to form subsequently a gel-like substance and function as a substitute for the vitreous. Among others silicone gels have been found to be suitable substitutes for the vitreous of the eye. These gels have been introduced into eyes of experimental animals to function as vitreous substitutes. They have proven to be useful substitutes since experimental animals treated with these gels have maintained their visual function. Furthermore, the gels are retained in the eyes for prolonged period of time. These gels also fulfill the need in the eye disorders of correcting vision problems resulting from cloudy or opaque vitreous after hemorrhages, inflammatory processes and repeated detachment. Furthermore, these gels can be employed in the treatment of retinal tears or detachments by supporting the retina.

The purpose of this invention is also to provide an intraocular support which can be left inside the eye for long periods of time indefinitely without emulsification and loss of clarity of the substance, eliminating the need for its removal, thus providing a permanent or semi-permanent intraocular support (specifically in eyes predisposed to hypotony). For this purpose silicone gels have been used, which can be injected initially in liquid form and permitted to congeal inside the vitreous cavity within a period of minutes to hours. After formation of the gel, the substance generally occupies the entire vitreous cavity (assuming shape of the eye cup) and will not move forward to come in contact with the cornea in aphakic eyes.

One class of the silicone substance that has been used is the type which can be cured after injection. This class of substance is silicone gels, which in the past have been used in the electronics industry, medical industry, and also has been applied as dental impression material. The experimental studies in the laboratory have demonstrated that silicone gel can be injected inside the animal eye without causing toxic reaction to the retina. The space-occupying effect provides support to the hypotonus eye, and the clarity of the substances permits light to reach the retina allowing it to function properly.

Accordingly, it is an objective of the invention to provide a vitreous substitute which gels inside the eye and does not emulsify when left in the eye for extended periods of time.

It is a further object of the present invention to use the vitreous substitute for treating ophthalmological disorders of the eye.

It is an object of the present invention to use the vitreous substitute which is capable of remaining in the eye for very long periods of time.

It is a still further object of the present invention to use the vitreous substitute which is transparent.

It is another object of the present invention to use the vitreous substitute which is capable of supporting the retina.

These and other objects and advantages of the present invention will become apparent to those skilled in the art after considering the following detailed specification.

DETAILED DESCRIPTION OF PREFERRED EMBODIMENTS

In its broadest aspect, the method of this invention involves the introduction of a gel-like composition, such as silicone gels, into the eye to treat ophthalmological disorders and to replace the vitreous. The gel can be introduced into the eye by different methods. Preferably, the gel components can be introduced separated, into the eye as liquid and then allowed to gel inside the vitreous cavity. Possible gel which may be used after laboratory purification is a silicone produced by General Electric Silicone which has the catalog reference number RTV 6196.

Although the gel components can be injected directly into the vitreous cavity, preferably a pars plana vitrectomy is performed to remove all the vitreous opacification and the traction bands. The retina is reattached by conventional means. The vitreous fluid can be replaced (initially with air) in case of silicone injection prior to injecting the mixture of the silicone gel. Because these materials are generally intended for permanent support of the retina in severely traumatized eyes, they need not be removed in the postoperative period. Because of the consistency of the gels and their softness, they provide gentle support to the retinal structure and prevent accumulation of fluid, cells and subsequent membrane formation, which is often seen with the use of silicone oil or other liquid materials (in dead spaces left between these materials and the retina).

The silicone gels are suitable substitutes for the vitreous. They can be advantageously designed to have similar physical properties of the vitreous being replaced. For example, volume, transparency, consistency, rigidity as well as viscoelasticity, i.e., viscosity and elasticity, can all be incorporated in the preparation of the gels. Among other advantages are that these gels have refractive indices close to that of water, and furthermore have the property of immiscibility with blood and water, cohesiveness and inertness. More importantly, the disadvantages observed with other present vitreous substitutes can be diminished with purified silicone gels.

Additionally, when the vitreous is removed a solution such as saline solution or perfluorocarbon liquid may be used to partially replace the vitreous and then the silicone gel may be poured into the eye on the surface of the saline solution or the perfluorocarbon liquid. Saline solution is used in the case where the retina is flat and perfluorocarbon liquid is used in the case where the retina needs to be flattended out. The amount of saline solution or perfluorocarbon liquid which may be used is 2 cc or an amount which fills half of the eye. The gel then forms a diaphram between the back of the eye and the front of the eye. This creates different chambers in the eye cavity and prevents diseases from the back of the eye to spread to the front part of the eye. An artificial diaphram is thus created in the vitreous cavity. Partially filling the eye cavity with a fluid silicone and silicone gel prevents stimulating factors to migrate toward the front of the eye (such as neovascularization of the iris) when the cristaline lens has been removed.

The invention, its principles and objectives will be further understood in view of the following examples. The following examples illustrate the use of gels in the eyes of experimental animals.

EXAMPLE 1

A single injection containing 1 ml of silicone and 1 ml of an initiator were introduced into the eye of an anesthetized monkey. The silicone and initiator used were purchased from General Electric Silicone, catalog number RTV 6196. The silicone preparations, which includes the silicone and the initiator, were was purified and then sterilized by filtration. A standard vitrectomy was performed leaving the cristaline lens in place. The vitreous fluid was replaced by air. The silicone and the initiator were mixed together and then injected using a small syringe and a 20 gauge needle into the vitreous cavity of the eye. The silicone usually gels at room temperature in about thirty minutes. However, since the body temperature of the animal is higher than room temperature, the silicone gelled within 10-30 minutes. The silicone was injected in liquid form and allowed to gel within the vitreous cavity of the eye. The monkey was kept in the supine position until the gel was formed. The gel was formed in about 10-20 minutes. Injecting in liquid form prevents the collaspe of the eye and holds the retina up, in place, preventing a retinal detachment. When the silicone gelled it conformed to the shape of the eye. The condition of the eye was good and no adverse effects have been observed to the retina or the cristaline lens. The eye and the back of the eye could be examined once the silicone gelled in the eye.

Although the silicone gel can be left in the eye permanently due to the fact that the silicone gel does not react with the ocular tissue, it is also possible to remove the gel from the eye. One method is to make an incision on the upper part of the cornea, similar to those performed for cataract extraction. A pronged foreign body forceps was used to remove the gel. The incision was then closed.

EXAMPLE II

The cristaline lens and the vitreous of a monkey were first removed then a fluid/air exchange was performed in which the vitreous fluid in the eye cavity replaced with air. The silicone and initiator used were purchased from General Electric Silicone, catalog number RTV 6196. The silicone was purified and sterilized by filtration. A single needle connected to a syringe containing 1 ml of silicone and 1 ml of the initiator were introduced into the eye of the anesthetized, monkey. The silicone and the initiator were injected in liquid form and allowed to fill the eye cavity until it reached the back surface of the iris. The monkey was kept in the supine position until the gel was formed. The gel was formed in about 10-20 minutes. The silicone gel did not damage the retina and did not migrate to the anterior chamber thus the cornea remains clear. A fundus examination was possible through the clear gel and no adverse effects have been observed.

There has been shown and described a novel vitreous substitute which fulfills all of the objects and advantages sought therefor. It will be apparent to those skilled in the art, however, that many changes, modifications, variations, and other uses and applications of the subject vitreous substitute are possible and contemplated. All such changes, modifications, variations, and other uses and applications which do not depart from the spirit and scope of this invention are deemed to be covered by the invention, which is limited only by the claims which follow.

What is claimed is:

1. A method of replacing the vitreous of an eye comprising the steps of:
   removing the vitreous from the vitreous cavity of the eye;
   replacing the vitreous with air;
   injecting an amount of silicone in liquid form into the vitreous cavity, the amount of silicone being sufficient to replace the air; and
   allowing the silicone to form a gel in the vitreous cavity.

2. The method of claim 1 wherein the vitreous is substantially replaced with the gel.

3. The method of claim 1 wherein the introduction of the silicone into the vitreous cavity and the withdrawal of the vitreous from the eye are conducted at the same time.

4. The method of claim 1 further comprising the step of purifying the silicone prior to injecting the silicone into the vitreous cavity.

5. A method of replacing the vitreous of an eye comprising the steps of:
   removing the vitreous from the vitreous cavity of the eye;
   replacing the liquid vitreous with air;
   injecting an amount of perfluorocarbon liquid into the vitreous cavity;
   injecting an amount of silicone in liquid form on the surface of the perfluorocarbon liquid; and
   allowing the silicone to form a gel in the vitreous cavity to develop a diaphram.

6. The method of claim 5 wherein the vitreous is substantially replaced with the gel and the perfluorocarbon liquid.

7. The method of claim 5 wherein the introduction of the perfluorocarbon liquid and the silicone in liquid form into the vitreous cavity and the withdrawal of the vitreous from the eye are conducted at the same time.

8. The method of claim 5 wherein the amount of perfluorocarbon liquid fills half of the vitreous cavity and the amount of silicone fills the other half of the vitreous cavity.

9. The method of claim 5 wherein the amount of perfluorocarbon liquid is injected into the vitreous cavity to flatten out the retina.

10. The method of claim 5 further comprising the step of purifying the silicone prior to injecting the silicone into the vitreous cavity.

11. A method of treating a retinal detachment of an eye comprising the steps of removing the vitreous from the eye, introducing into the eye under treatment a liquid comprising a liquid silicone in an amount effective to treat the retinal detachment and allowing the silicone liquid to form a gel in the eye.

12. The method of claim 11 further comprising the step of introducing into the eye an amount of saline solution prior to the step of introducing the liquid comprising the liquid silicone.

13. The method of claim 12 wherein the amount of saline solution fills half of the vitreous cavity of the eye and the amount of silicone fills the other half of the vitreous cavity of the eye.

14. The method of claim 12 wherein the amount of saline solution is 2 cc.

15. The method of claim 11 further comprising the step of purifying the silicone prior to introducing the silicone into the eye.

* * * * *